(12) United States Patent
Chasen

(10) Patent No.: US 6,660,060 B2
(45) Date of Patent: Dec. 9, 2003

(54) AIR FILTERING SYSTEM

(75) Inventor: James E. Chasen, West Haven, CT (US)

(73) Assignee: HP Intellectual Corp., Wilmington, DE (US)

(*) Notice: Subject to any disclaimer, the term of this patent is extended or adjusted under 35 U.S.C. 154(b) by 0 days.

(21) Appl. No.: 10/045,932

(22) Filed: Jan. 9, 2002

(65) Prior Publication Data
US 2003/0126986 A1 Jul. 10, 2003

(51) Int. Cl.⁷ ............................................. B01D 39/00
(52) U.S. Cl. .......................... 95/1; 96/222; 96/397; 55/482; 261/115; 4/213
(58) Field of Search .................. 96/222, 397; 55/482, 55/486; 261/115; 95/1; 4/213, 217, 228.1

(56) References Cited

U.S. PATENT DOCUMENTS

| | | |
|---|---|---|
| 2,860,725 A | 11/1958 | Cawl et al. |
| 2,911,062 A | 11/1959 | Ferraria |
| 3,745,965 A | 7/1973 | Ljung et al. ................. 116/112 |
| 4,001,912 A | 1/1977 | Eriksson ....................... 15/339 |
| 4,184,225 A | 1/1980 | Leinfelt ....................... 15/339 |
| 4,541,847 A * | 9/1985 | Oie et al. ....................... 96/58 |
| 5,192,424 A | 3/1993 | Beyne et al. ................. 210/85 |
| 5,294,407 A | 3/1994 | Succi et al. .................. 422/119 |
| 5,378,254 A | 1/1995 | Maly et al. ..................... 55/271 |
| 5,413,097 A | 5/1995 | Birenheide et al. ..... 128/206.17 |
| 5,454,122 A * | 10/1995 | Bergeron ........................ 4/217 |
| 5,674,381 A | 10/1997 | Den Dekker ................ 210/85 |
| 5,772,732 A | 6/1998 | James et al. ................... 95/25 |
| 5,810,908 A | 9/1998 | Gray et al. ..................... 95/25 |
| 5,907,886 A | 6/1999 | Buscher ....................... 15/319 |
| 5,914,453 A | 6/1999 | James et al. ................... 95/14 |
| 5,920,043 A | 7/1999 | Wang et al. .............. 200/52 R |
| 6,051,144 A | 4/2000 | Clack et al. ................. 210/739 |
| 6,073,302 A | 6/2000 | Buscher ....................... 15/339 |
| 6,077,336 A | 6/2000 | Ulrich et al. ................. 96/222 |
| 6,106,705 A | 8/2000 | Giordano et al. ............. 210/87 |
| 6,186,140 B1 | 2/2001 | Hoague .................. 128/202.22 |
| 6,214,239 B1 | 4/2001 | Renau ........................ 210/739 |
| 6,217,641 B1 | 4/2001 | Gunnarsson ................. 96/404 |

FOREIGN PATENT DOCUMENTS

| | | | |
|---|---|---|---|
| JP | 63129247 A | * | 6/1988 |
| JP | 04055637 A | * | 2/1992 |

* cited by examiner

Primary Examiner—Robert Hopkins
(74) Attorney, Agent, or Firm—Barry E. Deutsch

(57) ABSTRACT

An air deodorizing assembly including a frame having a liquid reservoir; a filter element connected to the frame; and a switch actuator connected to the frame. The switch actuator is adapted to cause an open electrical path to close when the frame is located proximate the open electrical path.

19 Claims, 2 Drawing Sheets

AIR FILTERING SYSTEM

BACKGROUND OF THE INVENTION

1. Field of the Invention

The present invention relates to air filtration and, more particularly, to a method and apparatus which comprises a removable air filter cartridge.

2. Prior Art

Some air filters have a unique shape which are designed to only fit the devices for which they were intended. This approach will not prevent operation of an air filtering apparatus in the event that the filter is not in place. This can cause product damage and reduce performance significantly. There is a need to provide a simple, low-cost method for preventing operation of an air filtering system in the event that the filter is not in place, or is not properly orientated, or the user is trying to install an improper filter.

SUMMARY OF THE INVENTION

In accordance with one aspect of the present invention, an air deodorizing assembly is provided including a frame having a liquid reservoir; a filter element connected to the frame; and a switch actuator connected to the frame. The switch actuator is adapted to cause an open electrical path to close when the frame is located proximate the open electrical path.

In accordance with another aspect of the present invention, a system for deodorizing air is provided comprising a housing; a fan connected to the housing; a removable air filter and liquid deodorizer cartridge connected to the fan; and an electrical circuit. The electrical circuit is connected to an electrical power supply for supplying electrical power to the fan. The cartridge and the electrical circuit form a switch in the electrical circuit which is closed by presence of the cartridge at a predetermined position in the housing. The switch is open when the cartridge is not located at the predetermined position in the housing. Operation of the fan is dependent upon the switch being closed such that proper positioning of the cartridge in the housing at the predetermined position is required in order to allow the fan to operate.

In accordance with one method of the present invention, a method of operating an air deodorizing system is provided comprising steps of inserting a removable combined air filter and liquid deodorizer reservoir cartridge into a housing of the air deodorizing system; and closing an open electrical path of an electrical circuit to a fan of the air deodorizing system when the cartridge is inserted into the housing in a predetermined position, the predetermined position comprising a magnet on the cartridge being located proximate a reed switch of the electrical circuit.

In accordance with another method of the present invention, a method of operating an air deodorizing system is provided comprising steps of inserting a removable filter cartridge into a housing of the air deodorizing system; and closing an open electrical path in an electrical circuit to a fan of the air deodorizing system when the cartridge is inserted into the housing in a predetermined position, the predetermined position comprising an electrical conductor on the cartridge contacting a pair of electrical contacts of the electrical circuit to close the open electrical path between the contacts.

BRIEF DESCRIPTION OF THE DRAWINGS

The foregoing aspects and other features of the present invention are explained in the following description, taken in connection with the accompanying drawings, wherein.

DETAILED DESCRIPTION OF THE PREFERRED EMBODIMENTS

Figure 1:
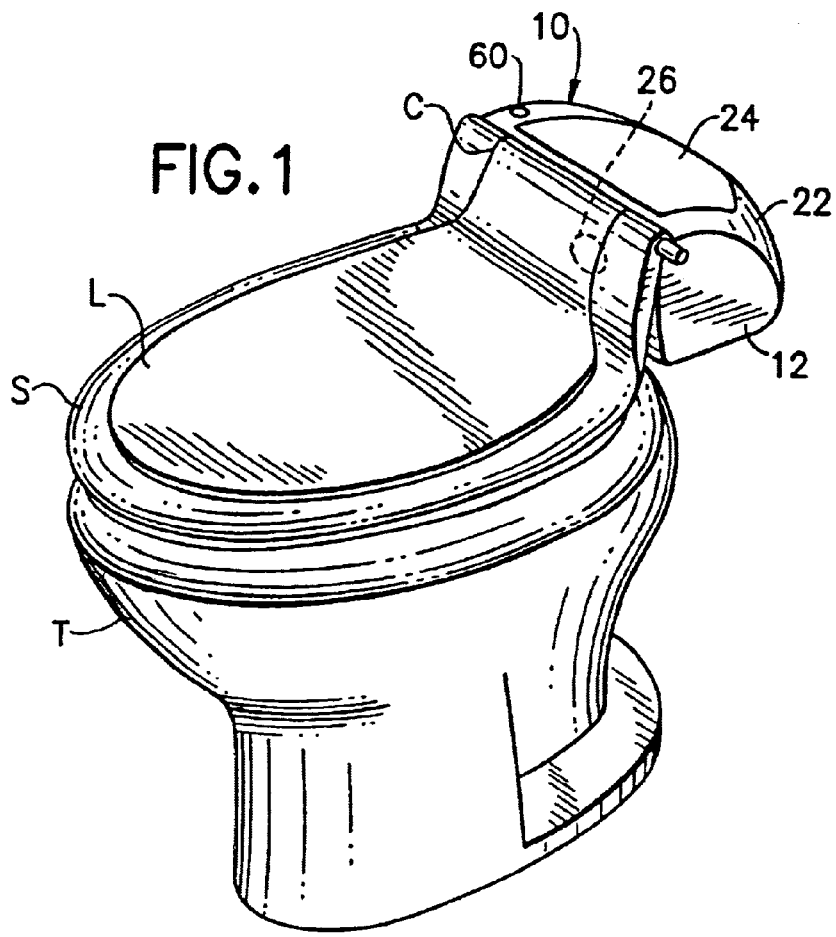
FIG. 1 is a perspective view of a toilet having a system for deodorizing air incorporating features of the present invention.

Referring to FIG. 1, there is shown a perspective view of a toilet bowl T having a deodorizing air system 10 incorporating features of the present invention. Although the present invention will be described with reference to the embodiments shown in the drawings, it should be understood that the present invention can be embodied in many alternate forms of embodiments. In addition, any suitable size, shape or type of elements or materials could be used.

Figure 2:
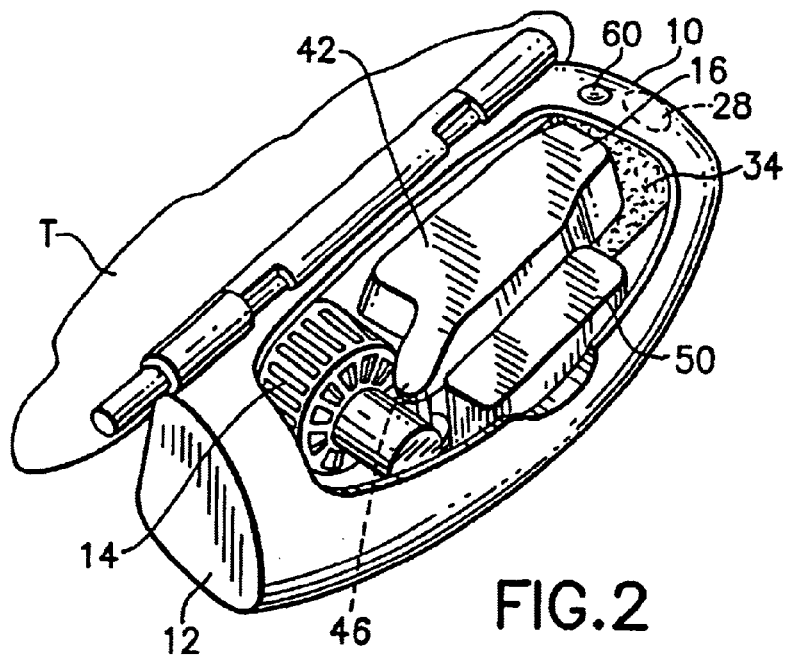
FIG. 2 is a perspective view of the deodorizing air system shown in FIG. 1 having its cover removed.
Figure 3:
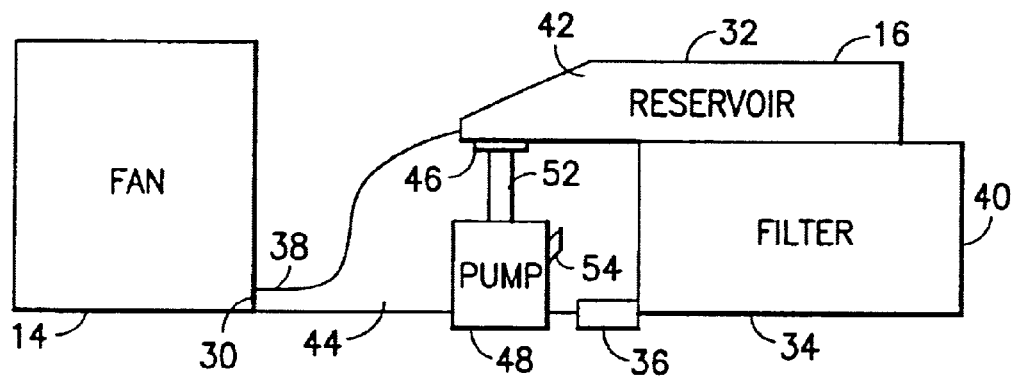
FIG. 3 is a block diagram of components of the deodorizing air system shown in FIG. 2.
Figure 4:
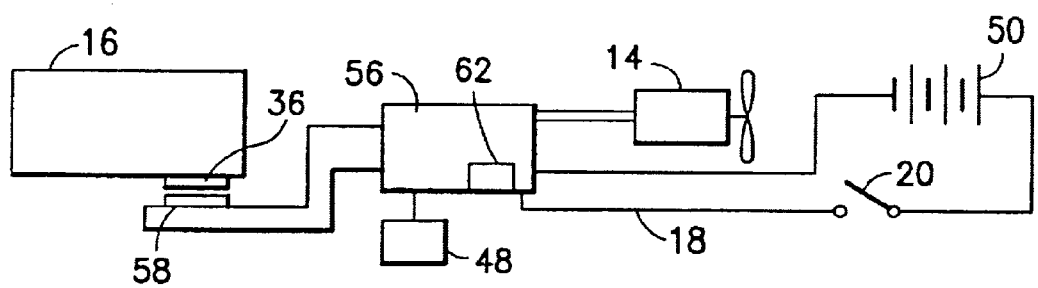
FIG. 4 is a schematic circuit diagram of components used in the deodorizing air system shown in FIG. 2.

Referring also to FIGS. 2–4, the deodorizing air system 10 generally comprises a housing 12, a fan 14, a removable combined air filter and liquid deodorizer cartridge 16, and an electrical circuit 18. In alternate embodiments, additional or alternative components could be provided. The housing 12 is preferably adapted to be mounted to the toilet bowl T at the back end of the toilet proximate the pivotal connection C of the toilet seat S and lid L. In a preferred embodiment, the seat S is biased in a slightly upward position relative to the toilet bowl T, such as by a spring. In this preferred embodiment, the electrical circuit 18 comprises a switch 20 which is adapted to be actuated when a person sits on the seat S. When a person sits on the seat S, the seat S is adapted to pivot downward against the toilet bowl T and close the switch.

The housing 12 comprises a main housing section 22 and a movable or removable lid 24. The main housing section 22 comprises an air entrance 26 at its front side. The air entrance 26 communicates with air from inside the toilet bowl T at a gap between the toilet bowl T and the mounting of the seat S and lid L at the connection C. The main housing section 22 also comprises an air outlet 28 at a lateral side. In alternate embodiments, the housing 12 could comprise any suitable shape or type of components.

The fan 14 generally comprises an electric fan with a front facing inlet located at the air entrance 26 and a lateral side facing outlet 30. In the embodiment shown, the fan 14 is a battery operated fan. However, in alternate embodiments, the fan 14 might not be battery operated, such as when the deodorizing air system 10 is connected to a main power supply. In addition, the inlet and outlet of the fan could be located at any suitable sides of the fan, such as when the fan is connected to suitable air duct conduits.

The cartridge 16 generally comprises a frame 32, a filter element 34, and a switch actuator 36. The cartridge 16 is adapted to be removably connected to the outlet 30 from the fan 14 inside the housing 12. The frame 32 generally comprises an air inlet 38, an air outlet 40, a liquid reservoir 42, and a chamber 44. The air inlet 38 is removably connected to the outlet 30. The filter element 34 is located at the opposite end of the air inlet 38, proximate the air outlet 40. The chamber 44 forms an open area between the inlet 38 and the filter element 34. The liquid reservoir 42 comprises an outlet 46. The liquid reservoir 42 is adapted to hold a supply of deodorizing liquid therein.

The filter element 34 is preferably a two-stage filter. However, in alternate embodiments, the filter element could comprise more or less than two stages. In a preferred embodiment, the filter element 34 comprises a polymer mesh filter first stage and an activated carbon filter second stage. However, in alternate embodiments, the different stages of the filter element 34 could comprise any suitable type of materials. In alternate embodiments, any suitable type of filter element(s) could be provided. The outlet from the second stage is located proximate the outlet 28 through the housing 12.

The chamber 44 is located between the inlet 38 and the filter element 34. The chamber 44 forms an area for air from the fan 14 to pass through into the filter element 34. The chamber 44 also forms an area for entry of liquid from the reservoir 42 into the air stream between the inlet 38 and the filter element 34.

The switch actuator 36 is fixedly attached to the frame 32 of the cartridge 16. In the embodiment shown, the switch actuator 36 comprises a permanent magnet. However, in alternate embodiments, the switch actuator 36 could comprise any suitable type of component. For example, in one alternate embodiment, the switch actuator 36 could comprise electrically conductive material used as an electrical contact. In another alternate embodiment, the switch actuator 36 could comprise a mechanical type of, actuator for actuating an electromechanical switch.

The deodorizing air system 10, in the embodiment shown, further comprises a liquid pump 48 and a battery 50. In an alternate embodiment, the liquid pump 48 could be replaced by a vacuum supply device or any other suitable type of liquid movement system for moving liquid from the reservoir 42 into the chamber 44. The liquid pump 48 is preferably battery operated. However, in alternate embodiments, the liquid pump could be actuated by any suitable type of drive system. For example, in one alternate embodiment, the pump 48 could be actuated by movement of the seat S. In another alternate embodiment, the pump 48 might not be provided, such as when liquid from the reservoir 42 is evacuated from the reservoir by the fan 14. In another alternate embodiment, the battery 50 might not be provided, such as when the deodorizing air system is powered by an electrical power supply other than a battery.

The liquid pump 48 comprises an inlet 52 which is adapted to mate with the outlet 46 of the reservoir 42. The pump 48 comprises an outlet or spray head 54. The outlet 54 extends into the chamber 44 for delivering liquid from the reservoir 42 into the chamber 44. Deodorizing liquid pumped into the chamber 44 by the liquid pump 48 will be atomized by the spray head 54 and picked up by the air stream passing through the chamber 44. The air stream, with entrained atomized deodorizing liquid, can then pass through the filter element 34 and exit out the outlet 28.

Referring particularly to FIG. 4, the electrical circuit 18 comprises the battery 50, the switch 20, the fan 14, the pump 48, a controller 56 and a switch 58. As noted above, the switch 20 is preferably actuated by movement of the seat S to a downward position. However, in alternate embodiments, the switch 20 might not be provided. In the embodiment shown, electrical circuit also comprises a manual override button or heavy duty button 60. The button 60 comprises a switch connected to the controller which, when manually depressed by a user, sends a signal to the controller.

In a preferred embodiment, the signal from the button 60 is sent to the controller 56 for signaling that the pump 48 should be actuated to add additional deodorizing liquid into the chamber 44 and/or that the fan 14 should continue to run for a predetermined period of time even if the switch 20 is open. In an alternate embodiment, the button 60 could merely be adapted to manually close the switch 20 without the seat S being moved to its down position. In another alternate embodiment, the manual override button 60 might not be provided.

The controller 56 preferably comprises a printed circuit board with a microprocessor 62. However, in alternate embodiments, the controller 56 could comprise any suitable type of component(s). In one type of alternate embodiment, the controller 56 could comprise merely an electromechanical switch. The controller 56 is adapted to actuate the fan 14 and the liquid pump 48.

When the switch 20 is closed, electricity from the battery 50 is supplied to the controller 56. When the controller 56 is supplied with electricity, the controller 56 does not automatically actuate the fan 14 and the liquid pump 48. Instead, before actuating the fan 14 and the liquid pump 48, the controller 56 first determines if the switch 58 has been actuated. Only if the switch 58 is actuated will the controller 56 allow electricity to be supplied to the fan 14 and liquid pump 48. Thus, only if the switch 58 is actuated will the controller allow the fan 14 and liquid pump 48 to operate.

The switch 58, in the embodiment shown, comprises a reed switch. The reed switch 58 is located adjacent a receiving area for receiving the cartridge 16. More specifically, the reed switch 58 is located directly opposite the switch actuator 36 when the cartridge 16 has been properly inserted into its receiving area in the housing 12. The reed switch 58 is normally maintained in an open position, but is adapted to be moved to a closed position by a magnetic field from the permanent magnet of the switch actuator 36. The reed switch 58 is adapted to be actuated or moved to a closed position by the permanent magnet of the switch actuator 36 when the switch actuator 36 is located directly opposite the reed switch. If the permanent magnet of the switch actuator 36 is not located directly opposite the reed switch 58, then the reed switch 58 remains in its deactuated or open position.

The interlock system of the present invention uses a small magnet which is attached at a predetermined location on the cartridge frame. When the cartridge is properly inserted into the device, the magnet moves in close proximity to the reed switch located off the controller printed circuit board. When the reed switch closes, it triggers a relay on the controller 56 which allows operation of the unit.

The controller 56 is adapted to sense whether the reed switch 58 is in its open position or its closed position. If the reed switch 58 is in its open position, the controller 56 will not cause the fan 14 and the pump 48 to operate. However, if the reed switch 58 is in its closed position, this signals that the cartridge 16 is located in the housing 12 and orientated in a proper position, and the controller 56 causes the fan 14 and pump 48 to operate. The system 10 requires both the switches 20, 58 to be closed before the system will operate. When both switches 20, 58 are closed, the fan 14 moves air from the bowl T, through the inlet 26, and into the chamber 44. The pump 48 delivers deodorizing liquid from the reservoir 42 into the chamber 44. The air and atomized liquid in the chamber 44 continue to flow through the flow path, through the filter element 34, and out the outlets 40, 28.

The present invention can prevent operation if the proper filter is not being used and can also prevent operation if the filter is not in place or orientated correctly. The present invention can use an interlock system which uses a small magnet that is attached at a predetermined location on the filter frame. When the filter is properly inserted into the device, the magnet can move in close proximity to a reed switch located off the control printed circuit board. When the reed switch closes, it can trigger a relay on the printed circuit board which allows operation of the unit. Use of the magnet and a reed switch configuration prevents the apparatus from being prone to problems relating to moisture or air contamination.

Figure 5:
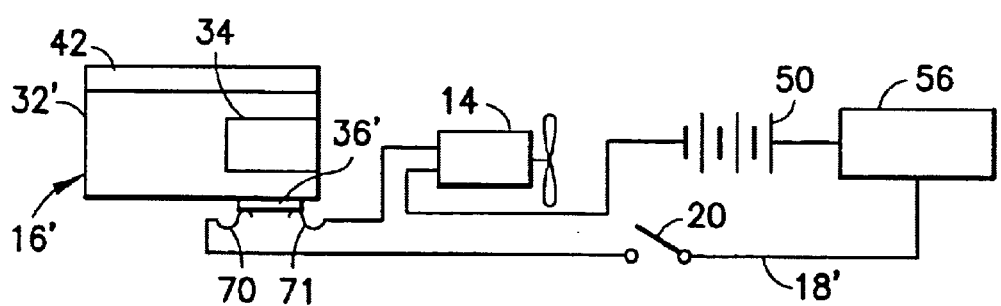
FIG. 5 is a schematic circuit diagram of an alternate embodiment of the present invention.

Referring now also to FIG. 5, an alternate embodiment of the deodorizing air system will be described. In this embodiment, the deodorizing air system generally comprises a fan 14, a removable cartridge 16', an electrical circuit 18', a power supply 50, and a controller 56. The electrical circuit 18' comprises the switch 20 and two electrical contacts 70, 71. The cartridge 16' generally comprises a frame 32', a filter element 34, and a switch actuator 36'. The cartridge 16' is adapted to be removably connected to the outlet 30 from the fan 14 inside the housing 12. The frame 32' generally comprises an air inlet, an air outlet, a liquid reservoir, and a chamber. The air inlet is removably connected to the outlet 30. The liquid reservoir 42 is adapted to hold a supply of deodorizing liquid therein.

The switch actuator 36', in the embodiment shown, comprises an electrical conductor attached to the exterior side of the frame 32'. In a preferred embodiment, the switch actuator 36' comprises a small piece of adhesive backed conductive tape. In an alternate embodiment, the switch actuator 36' could comprise a conductive stamped metal strip which is riveted, screwed or otherwise fastened into position onto the filter frame 32'. The adhesive tape is applied to a predetermined location on the filter frame.

The two contacts 70, 71 form an open circuit to the fan 14. When the cartridge 16' is properly located inside the housing, the switch actuator 36' makes electrical contact with the two contacts 70, 71. Thus, when the cartridge 16' is properly located inside the housing, the switch actuator 36' can close the open circuit between the two contacts 70, 71. When the cartridge is properly inserted into the device, the conductive tape bridges the gap between the two low voltage electrical contacts. The completed closed circuit can either be used to trigger a relay on the controller 56 or, if the current is low enough, directly power the blower motor. When the switch actuator 36' closes the open path between the contacts 70, 71, the controller 56 can actuate the fan 14 when the switch 20 is closed.

If the cartridge 16' is not properly located inside the housing, the open circuit between the two contacts 70, 71 prevents the fan 14 from operating. Therefore, only when the cartridge 16' is properly located in the housing of the deodorizing air system is the fan 14 allowed to operate. If the cartridge 16 is improperly located in the deodorizing air system housing, or no cartridge is located inside the housing, then the deodorizing air system will not function. This prevents the fan 14 from moving air out of the bowl T without the cartridge 16' being properly operationally inserted in the deodorizing air system housing, thus, preventing the deodorizing air system from moving unfiltered air out of its housing. In alternate embodiments, any suitable type of the interlock or signaling system for preventing the deodorizing air system from operating unless the combined air filter and liquid deodorizer cartridge is properly inserted could be provided. Features of the present invention can be applied to other products, such as a room air purifier.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. An air deodorizing assembly comprising:
    a frame comprising a liquid deodorizer reservoir;
    a filter element connected to the frame; and
    a switch actuator connected to the frame, wherein the switch actuator is adapted to cause an open electrical path to close when the frame is located proximate the open electrical path.

2. An air filter assembly as in claim 1 wherein the filter element comprises a two-stage filter assembly.

3. An air filter assembly as in claim 1 wherein the switch actuator comprises a magnet connected to the frame.

4. An air filter assembly as in claim 1 wherein the switch actuator comprises a conductor located on the frame.

5. An air filter assembly as in claim 1 further comprising deodorizer liquid located in the liquid deodorizer reservoir.

6. An air filter assembly as in claim 5 wherein the frame comprises an outlet from the liquid reservoir, the outlet being adapted to be connected to a pump.

7. A system for deodorizing air comprising:
    a housing;
    a fan connected to the housing;
    a removable combined air filter and liquid deodorizer cartridge connected to the fan; and
    an electrical circuit, connected to an electrical power supply, for supplying electrical power to the fan,
    wherein the cartridge and the electrical circuit form a switch in the electrical circuit which is closed by presence of the cartridge at a predetermined position in the housing, wherein the switch is open when the cartridge is not located at the predetermined position in the housing, and wherein operation of the fan is dependent upon the switch being closed such that proper positioning of the cartridge in the housing at the predetermined position is required in order to allow the fan to operate.

8. A system for deodorizing air as in claim 7 wherein the electrical circuit further comprises a switch which is adapted to be connected to a toilet bowl seat.

9. A system for deodorizing air as in claim 7 wherein the removable cartridge comprises a deodorizing liquid reservoir having liquid deodorizer therein.

10. A system for deodorizing air as in claim 9 further comprising a pump connected to the liquid reservoir, the pump being adapted to spray deodorizing liquid from the reservoir into an air path of the removable cartridge.

11. A system for deodorizing air as in claim 7 wherein the switch comprises a magnet on a frame of the removable cartridge and a reed switch in the electrical circuit.

12. A system for deodorizing air as in claim 7 wherein the switch comprises a conductor on a frame of the removable cartridge and the electrical contacts in the electrical circuit which are contacted by the conductor when the cartridge is positioned at the predetermined position.

13. A system for deodorizing air as in claim 7 further comprising a battery, the battery forming the electrical power supply.

14. A method of operating an air deodorizing system comprising steps of:
    inserting a removable combined air filter and liquid deodorizer reservoir cartridge into a housing of the air deodorizing system; and
    closing an open electrical path of an electrical circuit to a fan of the air deodorizing system when the cartridge is inserted into the housing in a predetermined position, the predetermined position comprising a magnet on the cartridge being located proximate a reed switch of the electrical circuit.

15. A method as in claim 14 wherein the step of inserting the removable cartridge into the housing comprises connecting an outlet from the liquid deodorizer reservoir of the cartridge to a deodorizer delivery system of the air filtering system.

16. A method as in claim 14 further comprising moving a toilet seat of a toilet to move a second switch of the electrical circuit to a closed position.

17. A method of operating an air deodorizing system comprising steps of:

inserting a removable combined air filter and liquid deodorizer reservoir cartridge into a housing of the air deodorizing system; and closing an open electrical path in an electrical circuit to a fan of the air deodorizing system when the cartridge is inserted into the housing in a predetermined position, the predetermined position comprising an electrical conductor on the cartridge contacting a pair of electrical contacts of the electrical circuit to close the open electrical path between the contacts.

18. A method as in claim 17 wherein the step of inserting the removable cartridge into the housing comprises connecting an outlet from the liquid deodorizer reservoir of the cartridge to a deodorizer delivery system of the air filtering system.

19. A method as in claim 17 further comprising moving a toilet seat of a toilet to move a second switch of the electrical circuit to a closed position.

* * * * *